(12) United States Patent
Ramirez

(10) Patent No.: US 8,952,057 B2
(45) Date of Patent: Feb. 10, 2015

(54) COMPOSITIONS FOR ANORECTAL USE AND METHODS FOR TREATING ANORECTAL DISORDERS

(75) Inventor: José E. Ramirez, Key West, FL (US)

(73) Assignee: JR Chem, LLC, Key West, FL (US)

( * ) Notice: Subject to any disclaimer, the term of this patent is extended or adjusted under 35 U.S.C. 154(b) by 182 days.

(21) Appl. No.: 13/161,992

(22) Filed: Jun. 16, 2011

(65) Prior Publication Data
US 2012/0177583 A1 Jul. 12, 2012

Related U.S. Application Data

(63) Continuation-in-part of application No. 13/004,465, filed on Jan. 11, 2011.

(51) Int. Cl.
| | | |
|---|---|---|
| A01N 55/02 | (2006.01) | |
| A61K 31/28 | (2006.01) | |
| A61K 31/315 | (2006.01) | |
| A61K 31/30 | (2006.01) | |
| A01N 33/00 | (2006.01) | |
| A61K 31/13 | (2006.01) | |
| A61K 31/16 | (2006.01) | |
| A01N 33/18 | (2006.01) | |
| A61K 33/24 | (2006.01) | |
| A61K 31/04 | (2006.01) | |
| A01N 37/00 | (2006.01) | |
| A61K 31/20 | (2006.01) | |
| A01N 25/00 | (2006.01) | |
| A61K 47/00 | (2006.01) | |
| A61K 51/00 | (2006.01) | |
| A61M 36/14 | (2006.01) | |
| A61F 9/02 | (2006.01) | |
| A61K 9/14 | (2006.01) | |
| A61K 9/00 | (2006.01) | |
| A61K 31/194 | (2006.01) | |
| A61K 31/198 | (2006.01) | |
| A61K 31/728 | (2006.01) | |
| A01N 55/04 | (2006.01) | |
| A61K 31/32 | (2006.01) | |
| A61K 31/295 | (2006.01) | |

(52) U.S. Cl.
CPC ............ *A61K 9/0031* (2013.01); *A61K 31/13* (2013.01); *A61K 31/194* (2013.01); *A61K 31/198* (2013.01); *A61K 31/28* (2013.01); *A61K 31/30* (2013.01); *A61K 31/315* (2013.01); *A61K 31/728* (2013.01); *Y10S 514/922* (2013.01); *Y10S 514/944* (2013.01); *Y10S 514/945* (2013.01); *Y10S 514/965* (2013.01); *Y10S 514/966* (2013.01)
USPC ........... 514/492; 514/494; 514/499; 514/500; 514/579; 514/740; 514/558; 514/781; 514/922; 514/944; 514/945; 514/965; 514/966; 514/493; 514/495; 514/501; 514/505; 424/1.61; 424/436; 424/488

(58) Field of Classification Search
USPC ......... 514/966, 492, 494, 499, 579, 922, 944, 514/945, 965; 424/1.61, 436, 488
See application file for complete search history.

(56) References Cited

U.S. PATENT DOCUMENTS

| | | |
|---|---|---|
| 46,494 A | 2/1865 | Pike |
| 51,868 A | 1/1866 | Schuster |
| 55,889 A | 6/1866 | Noll |
| 81,008 A | 8/1868 | Roemheld |
| 81,711 A | 9/1868 | Van Wagenen |
| 87,343 A | 3/1869 | Johnson |
| 88,973 A | 4/1869 | McDowell |
| 92,065 A | 6/1869 | Lighthall |
| 93,300 A | 8/1869 | Hall et al. |
| 116,875 A | 7/1871 | Shannon |
| 124,751 A | 3/1872 | Lauer |
| 127,925 A | 6/1872 | Roskopf |
| 128,385 A | 6/1872 | Goffinet |
| 145,749 A | 6/1873 | Pawlewski et al. |
| 140,768 A | 7/1873 | Fisher |
| 143,133 A | 9/1873 | Fehr |
| 149,857 A | 4/1874 | Halpen |
| 171,875 A | 1/1876 | Sievers |
| 173,607 A | 2/1876 | Fehr |
| 209,331 A | 10/1878 | Daniel |
| 229,014 A | 6/1880 | Sharetts |
| 232,807 A | 10/1880 | Dennett |
| 238,015 A | 2/1881 | Yater |
| 264,783 A | 9/1882 | Squier |
| 277,221 A | 5/1883 | Buse |
| 284,335 A | 9/1883 | Scott |
| 318,468 A | 5/1885 | Haley |
| 320,836 A | 6/1885 | Bisaillon |

(Continued)

FOREIGN PATENT DOCUMENTS

| | | |
|---|---|---|
| CA | 2376803 | 1/2001 |
| JP | 2001039809 | 2/2001 |

(Continued)

OTHER PUBLICATIONS

U.S. Appl. No. 13/004,465, filed Jan. 2011, Ramirez, J.*
International Search Report from International Application No. PCT/US2012/020466 mailed May 4, 2012.
Ruiz-Pérez, et al.. "Malonic Acid: a multi-modal bridging ligand for new architectures and properties on molecule-based magnets" *Polyhedron* 22 (2003) pp. 2111-2123.
Pasán, J., et al., "Malonate-based copper(II) coordination compounds: Ferromagnetic coupling controlled by dicarboxylates", *Polyhedron* 22 (2003) pp. 2143-2153.
Rodríguez-Martín Y., "Alternating cationic-anionic layers in the [MII(H$_2$O)$_6$][Cu$^{11}$(mal)$_2$(H$_2$O)] complexes linked through hydrogen bonds (M = Mn, Co, Ni, Cu and Zn; H$_2$mal = Malonic acid)", *CrystEngComm*, 2002, vol. 4, No. 107, 631.

(Continued)

*Primary Examiner* — David J Blanchard
*Assistant Examiner* — Helen Chui
(74) *Attorney, Agent, or Firm* — Carter, DeLuca, Farrell & Schmidt, LLP

(57) ABSTRACT

Compositions containing polymetal complexes are useful in treating anorectal disorders.

21 Claims, No Drawings

(56) References Cited

U.S. PATENT DOCUMENTS

| | | |
|---|---|---|
| 411,657 A | 9/1889 | Grosbety |
| 415,208 A | 11/1889 | Johson |
| 430,048 A | 6/1890 | Wainwright |
| 432,611 A | 7/1890 | Hall |
| 627,296 A | 6/1899 | Camnitzer |
| 928,539 A | 7/1909 | Pucciarelli |
| 944,738 A | 12/1909 | Loose |
| 992,937 A | 5/1911 | Brodbeck et al. |
| 1,059,841 A | 4/1913 | Crookes |
| 1,086,900 A | 2/1914 | David |
| 1,332,190 A | 2/1920 | Hull |
| 1,411,577 A | 4/1922 | Mullins et al. |
| 1,488,097 A | 3/1924 | Creger |
| 1,584,373 A | 5/1926 | Holzapfel |
| 1,593,485 A | 7/1926 | Crosnier |
| 1,627,963 A | 5/1927 | Fuller |
| 1,809,082 A | 6/1931 | Urkov et al. |
| 1,908,176 A | 5/1933 | Osterberg |
| 1,947,568 A | 2/1934 | Noonan |
| 1,949,797 A | 3/1934 | Kaufmann |
| 1,982,148 A | 11/1934 | Zimbron, Jr. |
| 2,002,829 A | 5/1935 | Osterberg |
| 2,054,989 A | 9/1936 | Moore |
| 2,087,162 A | 7/1937 | Moore |
| 2,095,092 A | 10/1937 | Barton |
| 2,114,490 A | 4/1938 | Harris |
| 2,129,836 A | 9/1938 | Goodman |
| 2,153,653 A | 4/1939 | Stux |
| 2,194,218 A | 3/1940 | Thurstan |
| 2,223,142 A | 11/1940 | Weirich |
| 2,241,331 A | 5/1941 | Shelton |
| 2,254,636 A | 9/1941 | Vangunten |
| 2,267,739 A | 12/1941 | Kemppe |
| 2,289,125 A | 7/1942 | Keil |
| 2,299,604 A | 10/1942 | Weirich |
| 2,344,830 A | 3/1944 | Mohs |
| 2,361,161 A | 10/1944 | Anderson |
| 2,370,561 A | 2/1945 | Mecca |
| 2,372,807 A | 4/1945 | Brown |
| 2,420,271 A | 5/1947 | Travis et al. |
| 2,420,389 A | 5/1947 | Travis et al. |
| 2,469,228 A | 5/1949 | Gertler |
| 2,527,686 A | 10/1950 | Sandberg |
| 2,556,567 A | 6/1951 | Wright |
| 2,602,039 A | 8/1952 | Wershaw |
| 2,649,398 A | 8/1953 | Wright et al. |
| 2,652,355 A | 9/1953 | Ercoli et al. |
| 2,673,364 A | 3/1954 | Diveley |
| 2,703,777 A | 3/1955 | Feinstein et al. |
| 2,736,681 A | 2/1956 | Tishler |
| 2,748,781 A | 6/1956 | Collat |
| 2,838,440 A | 6/1958 | Thurmon |
| 2,843,522 A | 7/1958 | Mahon |
| 2,846,322 A | 8/1958 | Buchalter |
| 2,870,150 A | 1/1959 | Wright et al. |
| 2,870,151 A | 1/1959 | Wright et al. |
| 2,872,372 A | 2/1959 | Hull |
| 2,991,224 A | 7/1961 | Bell |
| 3,013,883 A | 12/1961 | Welcker et al. |
| 3,033,755 A | 5/1962 | Jacobi |
| 3,035,988 A | 5/1962 | Cohen |
| 3,084,105 A | 4/1963 | Slodki |
| 3,137,622 A | 6/1964 | Mueller et al. |
| 3,146,168 A | 8/1964 | Battista |
| 3,164,523 A | 1/1965 | Fox et al. |
| 3,184,376 A | 5/1965 | Degoli |
| 3,210,248 A | 10/1965 | Feldmann et al. |
| 3,215,599 A | 11/1965 | Thau et al. |
| 3,255,079 A | 6/1966 | Schroeder et al. |
| 3,290,218 A | 12/1966 | de Jong |
| 3,317,372 A | 5/1967 | Hart |
| 3,366,114 A | 1/1968 | Kanter |
| 3,590,123 A | 6/1971 | Melloh et al. |
| 3,749,772 A | 7/1973 | Cardarelli et al. |
| 3,821,370 A | 6/1974 | Tenta |
| 3,821,371 A | 6/1974 | Battista |
| 3,826,845 A | 7/1974 | Suyama et al. |
| 3,856,941 A | 12/1974 | Turner |
| 3,896,238 A | 7/1975 | Smith |
| 3,903,268 A | 9/1975 | Balassa |
| 3,949,072 A | 4/1976 | Tenta |
| 4,048,300 A | 9/1977 | Tomlinson et al. |
| 4,054,596 A | 10/1977 | Koshar et al. |
| 4,062,937 A | 12/1977 | Rea |
| 4,100,269 A | 7/1978 | Pader |
| 4,129,510 A | 12/1978 | Smith |
| 4,138,477 A | 2/1979 | Gaffar |
| 4,146,607 A | 3/1979 | Ritchey |
| 4,154,911 A | 5/1979 | Bak et al. |
| 4,160,821 A | 7/1979 | Sipos |
| 4,161,526 A | 7/1979 | Gorman |
| 4,166,108 A | 8/1979 | Brown et al. |
| 4,226,851 A | 10/1980 | Sompayrac |
| 4,226,889 A | 10/1980 | Yuhas |
| 4,229,430 A | 10/1980 | Fahim et al. |
| 4,229,437 A | 10/1980 | Likens et al. |
| 4,255,418 A | 3/1981 | Bailey |
| 4,273,763 A | 6/1981 | Horrobin |
| 4,285,967 A | 8/1981 | Gubernick et al. |
| 4,291,025 A | 9/1981 | Pellico |
| 4,298,601 A | 11/1981 | Howard |
| 4,302,447 A | 11/1981 | Horrobin |
| 4,305,842 A | 12/1981 | Asakawa et al. |
| 4,309,989 A | 1/1982 | Fahim |
| 4,310,516 A | 1/1982 | Chang et al. |
| 4,315,916 A | 2/1982 | Likens et al. |
| 4,322,400 A | 3/1982 | Yuhas |
| 4,330,527 A | 5/1982 | Arima et al. |
| 4,331,653 A | 5/1982 | Brown et al. |
| 4,335,110 A | 6/1982 | Collins |
| 4,349,536 A | 9/1982 | Hausler |
| 4,372,296 A | 2/1983 | Fahim |
| 4,375,968 A | 3/1983 | Manhart |
| 4,376,115 A | 3/1983 | McCrorey |
| 4,395,398 A | 7/1983 | Yamamoto |
| 4,406,881 A | 9/1983 | Ladanyi |
| 4,428,933 A | 1/1984 | King |
| 4,430,324 A | 2/1984 | Viccaro |
| 4,444,755 A | 4/1984 | Horrobin |
| 4,465,666 A | 8/1984 | Lukas et al. |
| 4,469,684 A | 9/1984 | Higgins et al. |
| 4,477,439 A | 10/1984 | D'Alelio |
| 4,486,488 A | 12/1984 | Pietsch et al. |
| 4,503,037 A | 3/1985 | Szijjarto et al. |
| 4,512,978 A | 4/1985 | Inwood |
| 4,515,779 A | 5/1985 | Elliott |
| 4,522,806 A | 6/1985 | Muhlemann et al. |
| 4,568,540 A | 2/1986 | Asano et al. |
| 4,604,234 A | 8/1986 | Fujii et al. |
| 4,606,920 A | 8/1986 | Walter |
| 4,622,248 A | 11/1986 | Leach et al. |
| 4,647,452 A | 3/1987 | Ritchey et al. |
| 4,652,444 A | 3/1987 | Maurer |
| 4,654,213 A | 3/1987 | Ramirez et al. |
| 4,661,354 A | 4/1987 | Finnerty |
| 4,665,054 A | 5/1987 | Pickart |
| 4,678,664 A | 7/1987 | Schmolka |
| 4,683,133 A | 7/1987 | Southard |
| 4,708,864 A | 11/1987 | Maurer |
| 4,713,242 A | 12/1987 | Trenzeluk |
| 4,760,051 A | 7/1988 | Pickart |
| 4,762,715 A | 8/1988 | Lukas et al. |
| 4,767,753 A | 8/1988 | Pickart |
| 4,797,392 A * | 1/1989 | Chernomorsky ............ 514/185 |
| 4,810,693 A | 3/1989 | Pickart |
| 4,816,254 A | 3/1989 | Moss |
| 4,830,716 A | 5/1989 | Ashmead |
| 4,847,083 A | 7/1989 | Clark |
| 4,849,211 A | 7/1989 | Schrauzer |
| 4,855,138 A | 8/1989 | Trenzeluk |
| 4,863,987 A | 9/1989 | Hoshino et al. |
| 4,874,361 A | 10/1989 | Obagi |
| 4,877,770 A | 10/1989 | Pickart |
| 4,895,727 A | 1/1990 | Allen |

(56) References Cited

U.S. PATENT DOCUMENTS

| | | |
|---|---|---|
| 4,911,932 A | 3/1990 | Clum et al. |
| 4,937,230 A | 6/1990 | Pickart |
| 4,938,969 A | 7/1990 | Schinitsky et al. |
| 4,956,354 A | 9/1990 | Gutierrez |
| RE33,512 E | 1/1991 | Ramirez et al. |
| 4,992,259 A | 2/1991 | Schiraldi et al. |
| 5,000,944 A | 3/1991 | Prencipe et al. |
| 5,023,237 A | 6/1991 | Pickart |
| 5,059,588 A | 10/1991 | Pickart |
| 5,075,019 A | 12/1991 | Evans et al. |
| 5,075,469 A | 12/1991 | Chevion |
| 5,079,010 A | 1/1992 | Natterer |
| 5,091,171 A | 2/1992 | Yu et al. |
| 5,091,193 A | 2/1992 | Enjolras et al. |
| 5,093,099 A | 3/1992 | Haishi et al. |
| 5,099,034 A | 3/1992 | Yoshida et al. |
| 5,104,644 A | 4/1992 | Douglas |
| 5,118,665 A | 6/1992 | Pickart |
| 5,120,831 A | 6/1992 | Pickart |
| 5,135,913 A | 8/1992 | Pickart |
| 5,145,838 A | 9/1992 | Pickart |
| 5,154,932 A | 10/1992 | Burba, III et al. |
| 5,164,367 A | 11/1992 | Pickart |
| 5,165,914 A | 11/1992 | Vlock |
| 5,166,176 A | 11/1992 | Obagi et al. |
| 5,174,990 A | 12/1992 | Douglas |
| 5,177,061 A | 1/1993 | Pickart |
| 5,209,932 A | 5/1993 | Nichols |
| 5,214,032 A | 5/1993 | Pickart |
| 5,227,156 A | 7/1993 | Wiese |
| 5,232,691 A | 8/1993 | Lemole |
| 5,240,696 A | 8/1993 | Van Der Ouderaa et al. |
| 5,244,651 A | 9/1993 | Kayane et al. |
| 5,258,183 A | 11/1993 | Grimberg |
| 5,310,546 A | 5/1994 | Douglas |
| 5,330,748 A | 7/1994 | Winston et al. |
| 5,330,749 A | 7/1994 | Giacin et al. |
| 5,348,943 A | 9/1994 | Pickart |
| 5,352,438 A | 10/1994 | N'Guyen et al. |
| 5,382,431 A | 1/1995 | Pickart |
| 5,385,727 A | 1/1995 | Winston et al. |
| 5,401,730 A | 3/1995 | Sauvage et al. |
| 5,424,077 A | 6/1995 | Lajoie |
| 5,439,863 A | 8/1995 | Bottcher et al. |
| 5,455,023 A | 10/1995 | Giacin et al. |
| 5,466,470 A | 11/1995 | Lajoie |
| 5,480,975 A | 1/1996 | Goldberg et al. |
| 5,482,720 A | 1/1996 | Murphy et al. |
| 5,484,597 A | 1/1996 | Slavtcheff et al. |
| 5,496,539 A | 3/1996 | Mobley et al. |
| 5,500,448 A | 3/1996 | Cummins et al. |
| 5,504,055 A | 4/1996 | Hsu |
| 5,547,676 A | 8/1996 | Rocher et al. |
| 5,550,183 A | 8/1996 | Pickart |
| 5,552,147 A | 9/1996 | Znaiden et al. |
| 5,554,375 A | 9/1996 | Pickart |
| 5,554,647 A | 9/1996 | Perricone |
| 5,582,817 A | 12/1996 | Otsu et al. |
| 5,597,550 A | 1/1997 | Mo |
| 5,597,552 A | 1/1997 | Herms et al. |
| 5,616,313 A | 4/1997 | Williams et al. |
| 5,622,724 A | 4/1997 | Bryce-Smith |
| 5,624,675 A | 4/1997 | Kelly |
| 5,631,013 A | 5/1997 | Bergmann et al. |
| 5,632,972 A | 5/1997 | Williams et al. |
| 5,645,840 A | 7/1997 | Lajoie et al. |
| 5,663,213 A | 9/1997 | Jones et al. |
| 5,686,083 A | 11/1997 | Chamness |
| 5,688,492 A | 11/1997 | Galley et al. |
| 5,690,967 A | 11/1997 | Yu et al. |
| 5,696,169 A | 12/1997 | Otsu et al. |
| 5,698,184 A | 12/1997 | Pickart |
| 5,707,609 A | 1/1998 | Mo |
| 5,708,023 A | 1/1998 | Modak et al. |
| 5,728,404 A | 3/1998 | Von Rheinbaben et al. |
| 5,747,005 A | 5/1998 | Barels et al. |
| 5,753,637 A | 5/1998 | Fried |
| 5,762,945 A | 6/1998 | Ashley et al. |
| 5,780,020 A | 7/1998 | Peterson et al. |
| 5,795,574 A | 8/1998 | Breton et al. |
| 5,798,121 A | 8/1998 | Cauwet et al. |
| 5,827,884 A | 10/1998 | Obagi et al. |
| 5,837,270 A | 11/1998 | Burgess |
| 5,855,873 A | 1/1999 | Yam |
| 5,858,335 A | 1/1999 | Lucas et al. |
| 5,858,371 A | 1/1999 | Singh et al. |
| 5,858,993 A | 1/1999 | Pickart |
| 5,861,143 A | 1/1999 | Peterson et al. |
| 5,861,144 A | 1/1999 | Peterson et al. |
| 5,861,145 A | 1/1999 | Lucas et al. |
| 5,861,146 A | 1/1999 | Peterson et al. |
| 5,861,147 A | 1/1999 | Dodd et al. |
| 5,871,718 A | 2/1999 | Lucas et al. |
| 5,871,719 A | 2/1999 | Lucas et al. |
| 5,874,067 A | 2/1999 | Lucas et al. |
| 5,874,070 A | 2/1999 | Trinh et al. |
| 5,879,666 A | 3/1999 | Lucas et al. |
| 5,882,638 A | 3/1999 | Dodd et al. |
| 5,886,184 A | 3/1999 | Dolling et al. |
| 5,888,515 A | 3/1999 | Albert et al. |
| 5,888,522 A | 3/1999 | Pickart |
| 5,897,854 A | 4/1999 | Lucas et al. |
| 5,897,855 A | 4/1999 | Trinh et al. |
| 5,897,856 A | 4/1999 | Trinh et al. |
| 5,904,921 A | 5/1999 | Bresson-Rival et al. |
| 5,911,976 A | 6/1999 | Trinh et al. |
| 5,928,631 A | 7/1999 | Lucas et al. |
| 5,928,658 A | 7/1999 | Kishida et al. |
| 5,928,659 A | 7/1999 | Moy |
| 5,935,608 A | 8/1999 | Fujikawa et al. |
| 5,942,214 A | 8/1999 | Lucas et al. |
| 5,948,390 A | 9/1999 | Nelson et al. |
| 5,951,990 A | 9/1999 | Ptchelintsev |
| 5,955,067 A | 9/1999 | Oge et al. |
| 5,961,993 A | 10/1999 | Boussouira et al. |
| 5,965,137 A | 10/1999 | Petrus |
| 5,965,610 A | 10/1999 | Modak et al. |
| 5,972,999 A | 10/1999 | Murad |
| 5,980,477 A | 11/1999 | Kelly |
| 5,994,403 A | 11/1999 | Donatiello |
| 5,997,600 A | 12/1999 | Dean |
| 6,019,976 A | 2/2000 | Bryant |
| 6,022,565 A | 2/2000 | Albert et al. |
| 6,030,605 A | 2/2000 | D'Ameila et al. |
| 6,037,386 A | 3/2000 | Modak et al. |
| 6,046,178 A | 4/2000 | Silvetti, Sr. |
| 6,060,079 A | 5/2000 | Freeman et al. |
| 6,071,543 A | 6/2000 | Thornfeldt |
| 6,083,490 A | 7/2000 | Ellis et al. |
| 6,086,666 A | 7/2000 | Noguchi et al. |
| 6,103,247 A | 8/2000 | Boussouira et al. |
| 6,103,273 A | 8/2000 | Antoun |
| 6,113,636 A | 9/2000 | Ogle |
| 6,121,254 A | 9/2000 | Saint-Leger |
| 6,123,925 A | 9/2000 | Barry et al. |
| 6,132,743 A | 10/2000 | Kuroda et al. |
| 6,143,318 A | 11/2000 | Gilchrist et al. |
| 6,149,947 A | 11/2000 | Hon et al. |
| 6,183,785 B1 | 2/2001 | Westfall |
| 6,190,407 B1 | 2/2001 | Ogle et al. |
| 6,191,167 B1 | 2/2001 | Yu et al. |
| 6,197,815 B1 | 3/2001 | Hsu |
| 6,200,580 B1 | 3/2001 | Horino et al. |
| 6,200,680 B1 | 3/2001 | Takeda et al. |
| 6,217,914 B1 | 4/2001 | Meisner |
| 6,221,403 B1 | 4/2001 | Nesbit |
| 6,224,896 B1 | 5/2001 | Redmond |
| 6,248,370 B1 | 6/2001 | Harris |
| 6,261,574 B1 | 7/2001 | Costello |
| 6,267,782 B1 | 7/2001 | Ogle et al. |
| 6,287,541 B1 | 9/2001 | Creeth et al. |
| 6,303,651 B1 | 10/2001 | Hersh |
| 6,322,588 B1 | 11/2001 | Ogle et al. |
| 6,322,820 B1 | 11/2001 | Simoneau |

(56) References Cited

U.S. PATENT DOCUMENTS

| | | |
|---|---|---|
| 6,331,567 B1 | 12/2001 | Watson et al. |
| 6,361,800 B1 | 3/2002 | Cooper et al. |
| 6,375,942 B1 | 4/2002 | Rico |
| 6,395,301 B1 | 5/2002 | Cantin |
| 6,416,744 B1 | 7/2002 | Robinson et al. |
| 6,426,424 B1 | 7/2002 | Ashmead et al. |
| 6,444,699 B2 | 9/2002 | Meisner |
| 6,451,294 B1 | 9/2002 | Simon |
| 6,471,972 B1 | 10/2002 | Bonte et al. |
| 6,475,526 B1 | 11/2002 | Smith |
| 6,517,849 B1 | 2/2003 | Seger et al. |
| 6,518,240 B1 | 2/2003 | Pedersen et al. |
| 6,521,265 B1 | 2/2003 | Patterson |
| 6,558,710 B1 | 5/2003 | Godfrey |
| 6,579,541 B2 | 6/2003 | Antelman |
| 6,582,684 B1 | 6/2003 | Abrahamson |
| 6,582,710 B2 | 6/2003 | Deckers et al. |
| 6,592,852 B1 | 7/2003 | Ryles et al. |
| 6,599,513 B2 | 7/2003 | Deckers et al. |
| 6,607,711 B2 | 8/2003 | Pedersen |
| 6,607,716 B1 | 8/2003 | Smith et al. |
| 6,627,178 B1 | 9/2003 | Cawthon |
| 6,660,306 B2 | 12/2003 | Peshoff |
| 6,663,852 B2 | 12/2003 | Simon |
| 6,680,073 B1 | 1/2004 | Tarbet |
| 6,682,720 B2 | 1/2004 | Ryles et al. |
| 6,696,071 B2 | 2/2004 | Kelly |
| 6,710,079 B1 | 3/2004 | Ashmead et al. |
| 6,726,919 B2 | 4/2004 | Pace et al. |
| 6,730,309 B2 | 5/2004 | Horino |
| 6,730,329 B1 | 5/2004 | Smith |
| 6,743,416 B2 | 6/2004 | Riedl |
| 6,750,209 B1 | 6/2004 | Hudson et al. |
| 6,773,698 B1 | 8/2004 | Melinte et al. |
| 6,780,439 B2 | 8/2004 | Wilk |
| 6,800,301 B2 | 10/2004 | Smith |
| 6,833,362 B2 | 12/2004 | Bowen, Jr. et al. |
| 6,844,012 B1 | 1/2005 | Forceville et al. |
| 6,849,277 B2 | 2/2005 | Roig |
| 6,855,341 B2 | 2/2005 | Smith |
| 6,858,201 B2 | 2/2005 | Pickart |
| 6,929,800 B2 | 8/2005 | Salman |
| 6,932,976 B2 | 8/2005 | Brooks |
| 6,939,568 B2 | 9/2005 | Burrell et al. |
| 6,942,878 B2 | 9/2005 | Ishii et al. |
| 6,949,248 B2 | 9/2005 | Nishihama |
| 6,949,249 B2 | 9/2005 | Healy et al. |
| 6,964,782 B1 | 11/2005 | Smith et al. |
| 6,979,468 B1 | 12/2005 | Pollard |
| 6,989,156 B2 | 1/2006 | Gillis |
| 6,992,203 B2 | 1/2006 | Trusovs |
| 7,008,647 B2 | 3/2006 | Burrell et al. |
| 7,014,870 B1 | 3/2006 | Hon et al. |
| 7,022,351 B2 | 4/2006 | Abdel-Monem et al. |
| 7,026,308 B1 | 4/2006 | Gavin et al. |
| 7,049,339 B2 | 5/2006 | Thomson |
| 7,129,375 B2 | 10/2006 | Abdel-Monem et al. |
| 7,141,689 B2 | 11/2006 | Abdel-Monem et al. |
| 7,220,426 B2 | 5/2007 | Abdel-Monem et al. |
| 7,687,650 B2 | 3/2010 | Ramirez et al. |
| 2001/0014356 A1 | 8/2001 | Yoshida et al. |
| 2001/0041193 A1 | 11/2001 | Meisner |
| 2002/0001629 A1 | 1/2002 | Voellmy |
| 2002/0031557 A1 | 3/2002 | Meisner |
| 2002/0114847 A1 | 8/2002 | Peshoff |
| 2002/0182244 A1 | 12/2002 | Jackson |
| 2003/0004564 A1 | 1/2003 | Elkins et al. |
| 2003/0026848 A1 | 2/2003 | Joshi |
| 2003/0035825 A1 | 2/2003 | Shiau et al. |
| 2003/0059484 A1 | 3/2003 | Bonte et al. |
| 2003/0068351 A1 | 4/2003 | Roig |
| 2003/0069369 A1 | 4/2003 | Belenkaya et al. |
| 2003/0072819 A1 | 4/2003 | Tao |
| 2003/0077304 A1 | 4/2003 | McCadden |
| 2003/0077332 A1 | 4/2003 | Godfrey |
| 2003/0082219 A1 | 5/2003 | Warren et al. |
| 2003/0082223 A1 | 5/2003 | Healy et al. |
| 2003/0099721 A1 | 5/2003 | Yoshida et al. |
| 2003/0118623 A1 | 6/2003 | De Paoli Ambrosi |
| 2003/0133991 A1 | 7/2003 | Monroe et al. |
| 2003/0138497 A1 | 7/2003 | Sakuma et al. |
| 2003/0161892 A1 | 8/2003 | McFarland |
| 2003/0166510 A1 | 9/2003 | Pickart |
| 2003/0190371 A1 | 10/2003 | Graaf et al. |
| 2003/0194446 A1 | 10/2003 | Akes et al. |
| 2003/0199488 A1 | 10/2003 | Trotta |
| 2003/0215412 A1 | 11/2003 | Waugh et al. |
| 2003/0215522 A1 | 11/2003 | Johnson et al. |
| 2003/0224023 A1 | 12/2003 | Faryniarz et al. |
| 2003/0224027 A1 | 12/2003 | Faryniarz et al. |
| 2004/0022863 A1 | 2/2004 | Hamtini |
| 2004/0028708 A1 | 2/2004 | Brooks |
| 2004/0033270 A1 | 2/2004 | Kropf et al. |
| 2004/0037910 A1 | 2/2004 | Hon et al. |
| 2004/0058011 A1 | 3/2004 | Petersson |
| 2004/0058015 A1 | 3/2004 | Tao |
| 2004/0062730 A1 | 4/2004 | Kurosawa et al. |
| 2004/0062817 A1 | 4/2004 | Peshoff |
| 2004/0076686 A1 | 4/2004 | Riesinger |
| 2004/0091551 A1 | 5/2004 | Damji |
| 2004/0101541 A1 | 5/2004 | Heffernan et al. |
| 2004/0109902 A1 | 6/2004 | McDonagh et al. |
| 2004/0131700 A1 | 7/2004 | Cifra et al. |
| 2004/0147189 A1 | 7/2004 | Smith et al. |
| 2004/0156875 A1 | 8/2004 | Fabre et al. |
| 2004/0157921 A1 | 8/2004 | Cifra et al. |
| 2004/0170701 A1 | 9/2004 | Carter |
| 2004/0170703 A1 | 9/2004 | Hoekstra et al. |
| 2004/0170712 A1 | 9/2004 | Sadek El Mogy |
| 2004/0175433 A1 | 9/2004 | Thomson |
| 2004/0185015 A1 | 9/2004 | Zhang et al. |
| 2004/0185074 A1 | 9/2004 | Faryniarz et al. |
| 2004/0202689 A1 | 10/2004 | Subramanyan et al. |
| 2004/0220100 A1 | 11/2004 | Waugh et al. |
| 2004/0253321 A1 | 12/2004 | Fechner et al. |
| 2004/0258769 A1 | 12/2004 | Barker et al. |
| 2005/0032751 A1 | 2/2005 | Wang et al. |
| 2005/0048010 A1 | 3/2005 | Klis et al. |
| 2005/0069506 A1 | 3/2005 | Katusic et al. |
| 2005/0069588 A1 | 3/2005 | Taal |
| 2005/0074425 A1 | 4/2005 | Waugh et al. |
| 2005/0079229 A1 | 4/2005 | Cawthon |
| 2005/0100571 A1 | 5/2005 | Keyes |
| 2005/0123620 A1 | 6/2005 | Chiou |
| 2005/0125014 A1 | 6/2005 | Duluco et al. |
| 2005/0136129 A1 | 6/2005 | Verheul-Koot et al. |
| 2005/0175719 A1 | 8/2005 | Sun et al. |
| 2005/0202054 A1 | 9/2005 | Faryniarz et al. |
| 2005/0234239 A1 | 10/2005 | Taillefer et al. |
| 2005/0238730 A1 | 10/2005 | Le Fur et al. |
| 2006/0029682 A1 | 2/2006 | Monroe et al. |
| 2006/0036007 A1 | 2/2006 | Hsieh et al. |
| 2006/0089407 A1 | 4/2006 | Maurer |
| 2006/0240123 A1* | 10/2006 | Armstrong .................. 424/642 |
| 2007/0032751 A1 | 2/2007 | Roman |
| 2007/0163465 A1 | 7/2007 | Anderson et al. |
| 2007/0184017 A1 | 8/2007 | Faryniarz et al. |
| 2007/0191620 A1 | 8/2007 | Ramirez et al. |
| 2007/0203354 A1 | 8/2007 | Ramirez et al. |
| 2008/0081077 A1* | 4/2008 | Faryniarz et al. ............ 424/630 |
| 2008/0194471 A1* | 8/2008 | Cutler .......................... 514/11 |
| 2008/0206159 A1 | 8/2008 | Tamarkin et al. |
| 2009/0176876 A1 | 7/2009 | Ramirez et al. |
| 2010/0144870 A1 | 6/2010 | Ramirez et al. |

FOREIGN PATENT DOCUMENTS

| | | |
|---|---|---|
| WO | WO 94/14408 | 7/1994 |
| WO | WO 94/15216 | 7/1994 |
| WO | WO 02/100383 | 12/2002 |
| WO | WO 2004/039238 A2 | 5/2004 |
| WO | WO 2006/055526 | 5/2006 |

(56) References Cited

FOREIGN PATENT DOCUMENTS

| WO | WO 2006/104396 A1 | 10/2006 |
|---|---|---|
| WO | WO 2007/089267 | 8/2007 |
| WO | WO 2008/152444 A2 | 12/2008 |

OTHER PUBLICATIONS

Hernández-Molina M., "A phase transition in the novel three-dimensional compound [Eu$_2$(mal)$_2$(H$_2$O)$_6$](H$_2$mal = malonic acid)", *J.Chem.Soc., Dalton Trans.* 2002, vol. 18, 3462.

Rodríguez-Martín, Y., "Structural Versatility of the Malonate Ligand as a Tool for Crystal Engineering in the Design of Molecular Magnets", *Cryst. Eng. Comm.* 2002, vol. 4, No. 87, 522-535.

Rodríguez-Martín, Y., "Combining coordination chemistry and hydrogen bonds: Synthesis, Crystal Structures and thermal behaviour of the complexes [MII(L)(bpy)(H$_2$O)$_n$]•(NO$_3$)$_2$ (M$^{11}$ = Cu and Ni, n = 1 or 2, L = malonamide, bipy = 2,2'-bipyridine)", *J. Coord. Chem.*, 2003, vol. 56, No. 3, pp. 181-191.

Sanchiz, J., "Ferromagnetic coupling in the malonato-bridged copper(II) chains {[Cu(Im)$_2$(mal)]}$_n$ and {[Cu(2-MeIm)$_2$(mal)]}$_n$ (H$_2$mal = Malonic Acid, Im = imidazole and 2-MeIm = 2-methylimidazole)", *New J. Chem.* 2002, vol. 26, 1624.

Rodríguez-Martín, Y., "The flexibility of molecular components as a suitable tool in designing extended magnetic systems", *Cryst. Eng. Comm.* 2002, vol. 4, No. 73, 440-446.

Ruiz-Pérez, C., "Dimensionally controlled hydrogen-bonded nanostructures: Synthesis, structure, thermal and magnetic behaviour of the tris-(chelated)nickel(II) complex [Ni(bipy)$_3$]Cl$_2$.5.5H$_2$O (bipy = 2,2'-bipyridine)", *Inorg. Chim. Acta.* 2002, vol. 336, 131-136.

Rodríguez-Martín, Y., "Extended network via hydrogen bond linkages of coordination compounds: Synthesis, crystal structure and thermal behavior of the complexes [MII(L)$_2$(NO$_3$)$_2$] (MII = Cu, Co) and [Ni(L)$_2$(H$_2$O)$_2$]•(NO$_3$)$_2$ (L = malonamide)", *Inorganica Chimica Acta*. vol. 328, 169-178 (2002).

Rodríguez-Martín, Y., "Synthesis, crystal structure and magnetic properties of [Cu(bpym)(mal)(H$_2$O)]•6H$_2$O and [Cu$_2$(bpym)(mal)$_2$(H$_2$O)$_2$]•4H$_2$O (bpym = 2,2'-bipyrimidine, H2mal = Malonic Acid)", *Inorganica Chimica Acta.* vol. 326, 20-26 (2001).

Delgado, F., "Alkali-Templated Malonate Copper (II) Complexes", *Acta Cryst.* A61, C358 (2005).

Naumov, P, et al., "The Crystal Structure of Copper (II) Malonate Trihydrate", CCACAA, vol. 75, No. 3, 701-711 (2002).

Filippova I.G., "Polymorphism of Coordination Compounds with Malonic Añid", *Moldavian Journal of the Physical Sciences*, 1 vol. 1, No. 3, 87-93 (2002).

Tinker, D. et al., "Role of Selected Nutrients in Synthesis, Accumulation, and Chemical Modification of Connective Tissue Proteins", *Physiolgical Reviews*, vol. 65, No. 3, 607-657 (1985).

Philip, B., et al., "Dietary Zinc & Levels of Collagen, Elastin & Carbohydrate Components of Glycoproteins of Aorta, Skin & Cartilage in Rats", *Indian J. Exp. Biol.*, vol. 16, 370-372 (1978).

Homsy, R. et al., "Characterization of Human Skin Fibroblasts Elastase Activity", *J. Invest. Dermatol*, vol. 91, 472-477 (1988).

Chen et al., "Preparation and Kinetics of the Thermal Decomposition of Nanosized CuC$_2$O$_4$-ZnC$_2$O$_4$ 2H$_2$O", Wuhan University Journal of Natural Sciences, vol. 11, No. 3, pp. 667-671, May 2006.

M.A. Gabal, "Kinetics of the Thermal Decomposition of CuC$_2$O$_4$-ZnC$_2$O$_4$ Mixture in Air", Thermochimica Acta 402 (2003) pp. 199-208.

Huang Lianrong et al., "Thermal Behavior of Kinetics of the Decomposition of CuC$_2$O$_4$-ZnC$_2$O$_4$ 2H$_2$O by Different Preparation Methods", Journal of South-Central University for Nationalities (Nat. Sci. Edition), vol. 23, No. 3, pp. 12-16, Sep. 2004. (English Abstract Only).

Niyazmatov, Agzamdzhan Akhtamovich et al.: "Process for obtaining a diagnostic reagent for detecting antigens and antibodies of infectious and other illnesses", (1994).

* cited by examiner

COMPOSITIONS FOR ANORECTAL USE AND METHODS FOR TREATING ANORECTAL DISORDERS

RELATED APPLICATION

This application is a continuation-in-part of co-pending U.S. Ser. No. 13/004,465 filed Jan. 11, 2011.

BACKGROUND

1. Technical Field

The present disclosure relates to compositions for anorectal use and methods for treating anorectal disorders. More particularly, the compositions for anorectal use include organic compounds containing at least two coordination elements selected from copper, silver, gold, aluminum, scandium, titanium, vanadium, chromium, manganese, iron, cobalt, nickel, zinc, gallium, yttrium, zirconium, niobium, molybdenum, technetrium, ruthenium, rhodium, palladium, cadmium, indium, tin and germanium. The organic compounds can be prepared by reacting a polyfunctional compound with two or more coordination elements.

2. Background of the Invention

In general, anal fissure (fissure-in-ano), anal ulcer, hemorrhoidal diseases, and levator spasm (proctalgia fugax) are relatively common benign conditions of the anorectal area which affect subjects, including humans, of all ages, races, and sexes. However, these conditions can be problematical and inconvenient to treat and painful to endure. An anal fissure or ulcer is a tear or ulcer of the mucosa or lining tissue of the distal anal canal. An anal fissure or ulcer can be associated with another systemic or local disease, but is more frequently present as an isolated finding. The typical idiopathic fissure or ulcer is confined to the anal mucosa and usually lies in the posterior midline, distal to the dentate line. An individual with an anal fissure or ulcer frequently experiences anal pain and bleeding, the pain being more pronounced during and after bowel movements.

Hemorrhoids are specialized vascular areas lying subjacent to the anal mucosa. Symptomatic hemorrhoidal diseases are manifested by bleeding, thrombosis and/or prolapse of the hemorrhoidal tissues. Commonly, internal hemorrhoidal tissue bulges into the anal canal during defecation and results in bleeding and pain. As the tissue enlarges, further bleeding, pain, prolapse and thrombosis can ensue. The thrombosis of hemorrhoids is yet another cause of bleeding and pain.

Levator spasm is a condition affecting women more frequently than men. This syndrome is characterized by spasticity of the levator ani muscle, a portion of the anal sphincter complex. The patient suffering from levator spasm may experience severe, episodic rectal pain. A physical exam may reveal spasm of the puborectalis muscle and pain may be reproduced by direct pressure on this muscle. Bleeding is normally not associated with this condition.

Current treatments of anorectal disorders include relieving sphincter spasm and include dilatation (under anesthesia) or cutting a part of the sphincter (lateral internal sphincterotomy). In addition, applications of heat, cold, witch hazel, topical anesthetics, topical steroids, stool softeners, and bed rest have also been prescribed to treat the anorectal disorder as well as the symptoms associated with the disorder. However, none of these approaches include the use of a composition which contains at least one polymetal complex as described herein.

SUMMARY

Accordingly, compositions for anorectal use which contain at least one polymetal complex are described in the present disclosure. The polymetal complex can be the reaction product of a polyfunctional compound with two or more coordination elements. The polyfunctional compound can be, for example, a polyfunctional acid or an amino acid. The coordination elements can be selected from copper, silver, gold, germanium, aluminum, scandium, titanium, vanadium, chromium, manganese, iron, cobalt, nickel, zinc, gallium, yttrium, zirconium, niobium, molybdenum, technetium, ruthenium, rhodium, palladium, cadmium, indium and tin. Methods of making such reaction products are also described.

The synthetic compositions are prepared for anorectal administration and may take the form of any gas, liquid, solid or combination thereof which is capable of being administered to the anorectal region of a subject. In embodiments, the compositions may also include suitable materials which allow the compositions to take the form of useful anorectal delivery devices such as suppositories, sprays, gels, creams, ointments, foams, aerosols, and the like.

In addition, the present disclosure describes methods for treating anorectal disorders which includes administering to an anorectal region of a subject in need of such treatment an effective amount of the compositions described herein.

DETAILED DESCRIPTION OF PREFERRED EMBODIMENTS

The present disclosure describes compositions for anorectal use which include at least one polymetal complex. The synthetic compositions are prepared for anorectal administration and may be used in methods for treating anorectal disorders.

As defined herein, the term "anorectal region" is meant to include both the anus and the rectum regions of a mammal. Particularly, the term includes the internal anal canal, the external anus, the anal sphincter and the lower rectum.

The term "anorectal disorder" is defined herein to include any disorder associated with an anal rectal disease, including, but not limited to, acute or chronic anal fissures, internally or externally thrombosed hemorrhoids, hemorrhoidal diseases, disorders associated with endoscopic hemorrhoidal ligation, levator spasms, constipation, and pain associated with any anorectal disorder.

The terms "treatment" and "treating" are meant to include, but not be limited to, changes in the subject's status. The changes may be either subjective or objective and may relate to features such as symptoms or signs of the disease or disorder receiving therapy. For example, if the patient notes decreased itching, reduced bleeding, reduced discomfort or decreased pain, then successful treatment has occurred. Similarly, if the clinician notes objective changes, such as by histological analysis of a biopsy sample, then treatment has also been successful. Alternatively, the clinician may note a decrease in the size of lesions or other abnormalities upon examination of the patient. This would also represent an improvement or a successful treatment. Prevention of deterioration of the recipient's status is also included by the term.

The term "subject" as used herein includes animals, such as a mammal, including a human.

The term "effective amount" means a dosage sufficient to produce a desired result. The desired result may comprise a subjective or objective improvement in the recipient of the dosage.

As described herein, a new approach for treating anorectal disorders includes administering to a subject in need of such treatment an effective amount of a composition which includes at least one polymetal complex. The polymetal complex can be the reaction product of a polyfunctional compound with two or more coordination elements. The preparation of reaction products of polyfunctional compounds with two or more coordination elements and compositions containing such reaction products are described.

The polyfunctional compound can be any compound that contains at least two functional groups that may complex with metal cations in solution. Among the functional groups that may be present include carboxylic acid groups and amino groups. Suitable polyfunctional compounds include, but are not limited to polyfunctional acids, polyfunctional amines and amino acids. Other suitable polyfunctional compounds will be readily envisioned by those skilled in the art reading the present disclosure. It should of course be understood that mixtures of polyfunctional compounds may be used.

Polyfunctional acids are primarily compounds having two or more carboxylic acid groups. Non-limiting examples of polyfunctional acids include maleic acid, fumaric acid, citraconic acid, itaconic acid, glutaconic acid, phthalic acid, isophthalic acid, terephthalic acid, cyclohexane dicarboxylic acid, citric acid, succinic acid, adipic acid, sebacic acid, azealic acid, malonic acid, dodecanedioic acid, 1,18-octadecanedioic acid, dimer acids (prepared from a mono-, di- or triunsaturated fatty acid, acid wax, acid anhydride grafted wax, or other suitable polycarboxylic acid reacting compound), alkenyl succinic acids (such as n-dodecenylsuccinic acid, docecylcucinic acid and octadecenylsuccinic acid). The polyfunctional acid can be present in acidic form, anhydride form, ionic form, salt form, or mixtures thereof.

It is also contemplated that the polyfunctional acid can be a naturally occurring or synthetic polymer that includes two or more functional groups per polymer molecule, such as, for example, two or more carboxylic acid groups. One such polymeric polyfunctional acid is hyaluronic acid, a polymer of disaccharides, themselves composed of D-glucuronic acid and D-N-acetylglucosamine, linked via alternating $\beta$-1,4 and $\beta$-1,3 glycosidic bonds. Hyaluronic acid has a large number of carboxylic acid groups available which can readily interact with a plurality of different coordination elements.

Amino acids may also be used as the polyfunctional compound. Amino acids are known to those skilled in the art and include at least a carboxylic acid functionality and an amino functionality. Suitable amino acids include naturally occurring amino acids and synthetic amino acids. Non-limiting examples of amino acids include, but are not limited to: aminopolycarboxylic acids (e.g., aspartic acid, $\beta$-hydroxyaspartic acid, glutamic acid, $\beta$-hydroxyglutamic acid, $\beta$-methylaspartic acid, $\beta$-methylglutamic acid, $\beta,\beta$-dimethylaspartic acid, $\gamma$-hydroxyglutamic acid, $\beta,\gamma$-dihydroxyglutamic acid, $\beta$-phenylglutamic acid, $\gamma$-methyleneglutamic acid, 3-aminoadipic acid, 2-aminopimelic acid, 2-aminosuberic acid and 2-aminosebacic acid); amino acid amides such as glutamine and asparagine; polyamino- or polybasic-monocarboxylic acids such as arginine, lysine, $\beta$-aminoalanine, $\gamma$-aminobutyrine, ornithine, citruline, homoarginine, homocitrulline, hydroxylysine, allohydroxylsine and diaminobutyric acid; other basic amino acid residues such as histidine; diaminodicarboxylic acids such as $\alpha,\alpha'$-diaminosuccinic acid, $\alpha,\alpha'$-diaminoglutaric acid, $\alpha,\alpha'$-diaminoadipic acid, $\alpha,\alpha'$-diaminopimelic acid, $\alpha,\alpha'$-diamino-$\beta$-hydroxypimelic acid, $\alpha,\alpha'$-diaminosuberic acid, $\alpha,\alpha'$-diaminoazelaic acid, and $\alpha,\alpha'$-diaminosebacic acid; imino acids such as proline, hydroxyproline, allohydroxyproline, $\gamma$-methylproline, pipecolic acid, 5-hydroxypipecolic acid, and azetidine-2-carboxylic acid; mono- or di-alkyl (typically $C_1$-$C_8$ branched or normal) amino acids such as alanine, valine, leucine, allylglycine, butyrine, norvaline, norleucine, heptyline, $\alpha$-methylserine, $\alpha$-amino-$\alpha$-methyl-$\gamma$-hydroxyvaleric acid, $\alpha$-amino-$\alpha$-methyl-$\delta$-hydroxyvaleric acid, $\alpha$-amino-$\alpha$-methyl-$\epsilon$-hydroxycaproic acid, isovaline, $\alpha$-methylglutamic acid, $\alpha$-aminoisobutyric acid, $\alpha$-aminodiethylacetic acid, $\alpha$-aminodiisopropylacetic acid, $\alpha$-aminodi-n-propylacetic acid, $\alpha$-aminodiisobutylacetic acid, $\alpha$-aminodi-n-butylacetic acid, $\alpha$-aminoethylisopropylacetic acid, $\alpha$-amino-n-propylacetic acid, aaminodiisoamyacetic acid, $\alpha$-methylaspartic acid, $\alpha$-methylglutamic acid, 1-aminocyclopropane-1-carboxylic acid, isoleucine, alloisoleucine, tert-leucine, $\beta$-methyltryptophan and $\alpha$-amino-$\beta$-ethyl-$\beta$-phenylpropionic acid; $\beta$-phenylserinyl; aliphatic $\alpha$-amino-$\beta$-hydroxy acids such as serine, $\beta$-hydroxyleucine, $\beta$-hydroxynorleucine, $\beta$-hydroxynorvaline, and $\alpha$-amino-$\beta$-hydroxystearic acid; $\alpha$-Amino, $\alpha$-, $\gamma$-, $\delta$- or $\epsilon$-hydroxy acids such as homoserine, $\gamma$-hydroxynorvaline, $\delta$-hydroxynorvaline and epsilon-hydroxynorleucine residues; canavine and canaline; $\gamma$-hydroxyornithine; 2.hexosaminic acids such as D-glucosaminic acid or D-galactosaminic acid; $\alpha$-Amino-$\beta$-thiols such as penicillamine, $\beta$-thiolnorvaline or $\beta$-thiolbutyrine; other sulfur containing amino acid residues including cysteine; homocystine, $\beta$-phenylmethionine, methionine, S-allyl-L-cysteine sulfoxide, 2-thiolhistidine, cystathionine, and thiol ethers of cysteine or homocysteine; phenylalanine, tryptophan and ring-substituted $\alpha$ amino acids such as the phenyl- or cyclohexylamino acids $\alpha$-aminophenylacetic acid, aaminocyclohexylacetic acid and $\alpha$-amino-$\beta$-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro, o-, m- or p-methyl-, 2,4,6-trimethyl-, 2-ethoxy-5-nitro-, 2-hydroxy-5-nitro- and p-nitrophenylalanine); furyl-, thienyl-, pyridyl-, pyrimidinyl-, purinyl- or naphthylalanines; and tryptophan analogues and derivatives including kynurenine, 3-hydroxykynurenine, 2-hydroxytryptophan and 4-carboxytryptophan; $\alpha$-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and $\alpha$-Hydroxy and substituted $\alpha$-hydroxy amino acids including serine, threonine, allothreonine, phosphoserine and phosphothreonine glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Aminopolycarboxylic acids, e.g., aspartic acid, $\beta$-hydroxyaspartic acid, glutamic acid, $\beta$-hydroxyglutamic acid, $\beta$-methylaspartic acid, $\beta$-methylglutamic acid, $\beta,\beta$-dimethylaspartic acid, $\gamma$-hydroxyglutamic acid, $\beta,\gamma$-dihydroxyglutamic acid, $\beta$-phenylglutamic acid, $\gamma$-methyleneglutamic acid, 3-aminoadipic acid, 2-aminopimelic acid, 2-aminosuberic acid and 2-aminosebacic acid. Polyaminoacids may also be used provided they form complexes with the coordination elements employed.

The polyfunctional compound is reacted with two or more coordination elements. The coordination elements can be chosen from the elements listed in Groups IIIA to VIIIA, Groups IB to IIIB, of periods 4 and 5 and aluminum in Group IIIB, period 3 of The Periodic Table of the Elements. Suitable non-limiting examples of elements listed in group IB of The Periodic Table of Elements include copper, silver, and gold. Suitable non-limiting examples of coordination elements include aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium. Tin may also be used. Those skilled in the area will readily envision suitable compounds for providing the coordination elements in solution.

In embodiments, a bimetal complex formed by an aqueous solution containing: a) one or more polycarboxylic acids, b) one or more polyamines and/or c) one or more amino acids having at least two carboxylic acid groups with two or more coordination elements selected from copper, silver, gold, aluminum, scandium, titanium, vanadium, chromium, manganese, iron, cobalt, nickel, zinc, gallium, yttrium, zirconium, niobium, molybdenum, technetium, ruthenium, rhodium, palladium, cadmium, indium and tin and germanium.

For example, water soluble salts containing the coordination element may be used. The salts may be organic or inorganic. Suitable water-soluble silver salts include silver nitrate, silver acetate, silver propionate, silver sulfate, silver butyrate, silver isobutyrate, silver benzoate, silver tartrate, silver salicylate, silver malonate, silver succinate and silver lactate. Suitable water-soluble aluminum salts include aluminum potassium sulfate, aluminum chloride, aluminum sodium sulfate, aluminum sodium phosphate, aluminum sulfate, aluminum nitrate, and sodium aluminate. Suitable water-soluble copper salts include copper sulfate, fluoroborate, hydroxide, borate, fluoride, carbonate, oxychloride, formate or acetate. Suitable water-soluble zinc salts include zinc chloride, zinc bromide, zinc iodide, zinc chlorate, zinc bromate, zinc chlorite, zinc perchlorate, zinc sulfate, zinc nitrate, zinc nitrite, zinc borate, zinc metaborate, basic zinc borate, zinc hexafluorosilicate, zinc hypophosphite, zinc glycerophosphate, zinc bichromate, zinc citrate, zinc thionate, zinc dithionate, zinc tetrathionate, zinc pentathionate, zinc thiocyanate, zinc benzoate, zinc acetate, zinc salicylate, zinc picrate, zinc permanganate, zinc hydrogen phosphate, zinc formate, zinc ethylsulfate and zinc phenolsulfonate. Examples of suitable water soluble nickel salts that may be used include nickel sulfate hexahydrate and nickel chloride hexahydrate. It should be understood that the listed salts are only a small portion of the salts suitable for use in accordance with the present disclosure. For example, inorganic salts are suitable provided that they provide coordination element cations when placed in an aqueous solution. Thus, the foregoing list of salts should be considered a non-limiting, illustrative list.

For carrying out the process, a reaction solution can be prepared by mixing the various ingredients in water. Water in the mixture may advantageously be added in limited amounts sufficient to allow the reaction product to precipitate from solution upon formation. Accordingly, the reaction mixture is not so dilute as to prevent product precipitate formation. Where necessary, mixing and heating can be used to bring the reactants to 40-100° C. in order to force the reaction. As a result, reactant solubility may be enhanced through energy input such as microwave heating or addition of boiling water. The input of the energy may take place through any instrument capable of heating the aqueous reaction mixture. The reaction products formed in solution may be immediately separated so that their production can take place in a continuous process. Where a short reaction time and rapid crystallization of the reaction product occur, the conversion may be carried out continuously, and the recovery of the resultant solid product may take place by any conventional manner such as filtering, centrifugation, or sedimentation.

In embodiments, the method of forming a polymetal complex includes forming a solution by adding to a solvent (i) at least one polyfunctional compound selected from polycarboxylic acids, polyamines and amino acids having at least two carboxylic acid groups and (ii) basic salts of two or more coordination elements selected from one or more of copper, silver, gold, aluminum, scandium, titanium, vanadium, chromium, manganese, iron, cobalt, nickel, zinc, gallium, yttrium, zirconium, niobium, molybdenum, technetium, ruthenium, rhodium, palladium, germanium, cadmium, and indium; and recovering a polymetal complex that includes the two or more coordination elements joined to a central unit derived from the polyfunctional compound.

The polyfunctional compound is present in the reaction mixture in amounts that will contact metal cations in an aqueous solution. Suitable amounts of polyfunctional compound also include excess amounts in relation to the amount of metal cations. In embodiments, polyfunctional compound is present in a 3:1:1 molar ratio in relation to the metal constituents. In embodiments, the polyfunctional compound is malonic acid which can be present in acidic form, salt form, or mixtures thereof. In embodiments, the process parameters are especially advantageous if the polyfunctional compound is added to excess in comparison to the metal counter cation constituents. Depending on the desired complex, the latter are added so that the molar ratio of polyfunctional compound to metal ions is approximately 3:2.

In embodiments, the coordination elements may be present as one or more ionic compounds formed by joining one or more independent coordination element molecules or ions of a first type and coordination element molecules or ions of a second type to a central unit by ionic bonds. For example, the reaction product may be in the form of a trinuclear cation, where structurally independent coordination element hydrates are bridged by a central unit. However, various coordination modes are possible depending on the source of the coordination elements and synthesis conditions. In embodiments, the central unit may be a multi-membered ring such as eight-membered ring, six-membered ring, and four-membered metalocycle for bridging or chelating functions between the coordination element constituents. Accordingly, the crystal structures of the reaction products can be very diverse, from ionic to three-dimensional polymers. In embodiments, the reaction products are present in several hydrate, and polymorphic forms.

In embodiments, the polymetal complex includes one or more molecules of a first coordination element, one or more molecules of a second coordination element different from the first coordination element, and a central unit, wherein the central unit includes at least one compound selected from polycarboxylic acids, polyamines and amino acids and the center unit bridges the one or more molecules of a first coordination element and one or more molecules of a second coordination element by coordinate bonding. In embodiments, the center unit is an amino acid having at least two carboxylic acid groups. In embodiments, the central unit includes a plurality of amino acids, either as a polyaminoacid, as a complex of associated amino acids, or as any other structure.

In embodiments, the polymetal complex is a chelate formed by a) at least one polyfunctional compound selected from polycarboxylic acids, polyamines and amino acids having at least two carboxylic acid groups with b) basic salts of two or more coordination elements selected from one or more of copper, silver, gold, aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium, wherein the chelate includes two or more coordination elements are joined to a central unit derived from the polyfunctional compound.

In embodiments, suitable reaction products can be non-toxic polymetal complexes that include copper, zinc, aluminum and/or silver constituents. Such copper, zinc, aluminum and/or silver reaction products include, but are not limited to water soluble compounds that contain copper, zinc, aluminum and/or silver. Non-limiting examples of water-soluble polymetal complexes include copper-zinc citrate, copper-silver citrate, silver-zinc citrate, copper-zinc oxalate, copper-silver oxalate, silver-zinc oxalate, copper-zinc tartarate, copper-silver tartarate, silver-zinc tartarate, copper-zinc malate, copper-silver malate, silver-zinc malate, copper-zinc succinate, copper-silver succinate, silver-zinc succinate, copper-zinc malonate, copper-silver malonate, silver-zinc malonate, copper-zinc maleate, copper-silver maleate, silver-zinc maleate, copper-zinc aspartate, copper-silver aspartate, silver-zinc aspartate, copper-zinc glutamate, copper-silver glutamate, silver-zinc glutamate, copper-zinc glutarate, copper-silver glutarate, silver-zinc glutarate, copper-zinc fumarate, copper-silver fumarate, silver-zinc fumarate, copper-zinc glucarate, copper-silver glucarate, silver-zinc glucarate, copper-zinc polyacrylic acid, copper-silver polyacrylic acid, silver-zinc polyacrylic acid, and combinations thereof. In embodiments, copper, zinc, aluminum and silver salts of organic multi carboxylic acids are suitable for use in accordance with the present disclosure. In embodiments, suitable salts can be doped such that the unit cell of the salt has zinc or silver constituents dispersed therein. Such zinc or silver constituents may either substitute another metallic constituent or fill a preexisting void in the unit cell.

In embodiments, suitable reaction products can be copper salts having zinc or silver constituents therein. For example, zinc or silver may either substitute a copper constituent or fill a preexisting void in the copper salt's unit cell. Suitable non-limiting examples of copper salts which may be used to form polymetallic complexes include copper (II) malonate and any hydrated form thereof such as copper (II) malonate dihydrate, copper (II) malonate trihydrate, and copper malonate tetrahydrate. Other suitable non-limiting examples of suitable copper salt active ingredients include copper citrate, copper oxalate, copper tartarate, copper malate, copper succinate, copper malonate, copper maleate, copper aspartate, copper glutamate, copper glutarate, copper fumarate, copper glucarate, copper polyacrylic acid, and combinations thereof. In embodiments, suitable copper salts can be doped such that the unit cell of the salt has zinc or silver constituents dispersed therein. Such zinc or silver constituents may either substitute a copper constituent or fill a preexisting void in the unit cell.

Cu/Zn Malonate Embodiments

In embodiments, malonic acid may be reacted with salts containing copper and zinc constituents in an aqueous solution. It has been found that where the malonic acid, copper and zinc constituents are present in at least about a 3:1:1 molar ratio, copper-zinc malonates may be produced in good yield and high crystalline purity.

Malonic acid refers to 1,3-propanedioic acid, a dicarboxylic acid with structure $CH_2(COOH)_2$ or:

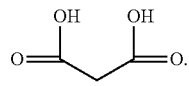

The ion form of malonic acid, as well as its esters and salts, are known as malonates. For example, diethyl malonate is ethyl ester of malonic acid. As used herein, the term copper-zinc malonate applies to any salt substances formed from malonic acid having copper and zinc constituents.

Suitable ingredients for the formation of copper-zinc malonates include malonic acid, one or more bases of copper and zinc, and water. In an aqueous reaction solution, suitable salt forms provide copper and zinc cations capable of bonding to malonate anions. Other suitable ingredients for the formation of copper-zinc malonates will include the replacement of bases of copper and zinc with the metallic form of copper and zinc. The elemental form of copper and zinc are known as copper and zinc metals and will be dissolved in the acidic water media as they react with malonic acid.

One or more salts containing copper and zinc constituents are present in amounts that will contact malonic acid in an aqueous solution. Suitable salts for making copper-zinc malonate compositions in accordance with this disclosure include metal salts containing complex-forming metal ions of copper and/or zinc. Non-limiting examples of suitable metal salts are copper (I) and (II) salts such as copper chloride, copper bromide, copper fluoride, copper nitrate, copper fluoroborate, copper sulfate, copper acetate, copper trifluoro acetate, copper stearate, copper octoate, copper methacrylate, copper malonate, copper benzoate; zinc salts such as zinc bromide, zinc chromate, zinc chloride, zinc stearate, zinc octoate, and zinc ethylhexoate. In embodiments, the aqueous solution may include one or more metallic salts, such as cupric carbonate ($CuCO_3.Cu(OH)_2$), zinc carbonate ($3Zn(OH)_2.2ZnCO_3$), metallic copper, metallic zinc and combinations thereof. Basic salts such as basic zinc salts, basic copper salts, and combinations thereof are also suitable for use in accordance with the present disclosure. In embodiments, suitable metal basic salts are: copper (I) and (II) salts such as copper carbonate, copper oxide, and copper hydroxide; and zinc salts such as zinc carbonate, zinc oxide, and zinc hydroxide.

It should be understood that the listed salts are only a small portion of the salts suitable for use in accordance with the present disclosure. For example, inorganic salts are suitable provided that they provide copper and zinc cations when placed in an aqueous solution. Thus, the foregoing list of salts should be considered a non-limiting, illustrative list.

For carrying out the process, the reaction solution can be prepared by mixing the various ingredients in water where malonic acid and the salts may ionize and become more reactive. Water in the mixture is added in limited amounts sufficient to allow copper-zinc malonates to precipitate from solution upon formation. Accordingly, the reaction mixture is not so dilute as to prevent product precipitate formation. Where copper and zinc salts in the reaction mixture are insoluble and form dispersions (such as at cooler temperatures), mixing and heating steps can be applied to bring the reactants to 40-100° C. in order to force the reaction. As a result, reactant solubility may be enhanced through energy input such as microwave heating or addition of boiling water dissolver. The input of the energy may take place through any instrument capable of heating the aqueous reaction mixture. The copper-zinc malonate complexes formed in solution may be immediately separated so that their production can take place in a continuous process. Due to the short reaction time and the rapid crystallization of the copper-zinc malonate product, the conversion may be carried out continuously, and the recovery of the resultant solid product may take place by any conventional manner such as filtering, centrifugation, or sedimentation.

In the production of the reaction mixture, the concentration of the polyfunctional compound and that of the copper and zinc constituents may be pre-selected so that the total concentration of product formed exceeds the solubility equilibrium. This will result in product precipitating from solution in solid form for easy collection.

In embodiments, the final composition may be a deep blue crystal having good yield and substantial crystalline purity. Suitable copper-zinc malonate forms in accordance with the present disclosure include any salt formed from the neutralization of malonic acid by one or more copper containing molecules and one or more zinc containing molecules. Illustrative examples include salt formed by the neutralization of malonic acid by cupric carbonate ($CuCO_3 \cdot Cu(OH)_2$), and zinc carbonate ($3Zn(OH)_2 \cdot 2ZnCO_3$) in an aqueous solution. Here copper may be added first, followed by zinc in order to obtain the salts of the present disclosure.

In embodiments, the copper-zinc malonates may be one or more ionic compounds formed by joining one or more independent copper molecules or ions and one or more independent zinc molecules or ions to a central unit by ionic bonds. For example, the copper-zinc malonate may be in the form of a trinuclear cation, where structurally independent copper and zinc hydrates are bridged by a central unit such as an octahedral diaquadimalonatocopper (II) unit. However, various coordination modes are possible depending on the source of the copper and zinc and synthesis conditions. In embodiments, the central unit malonate ion may be a multi-membered ring such as eight-membered ring, six-membered ring, and four-membered metalocycle for bridging or chelating functions between the copper and zinc constituents. Accordingly, the crystal structures of copper-zinc malonates can be very diverse, from ionic to three-dimensional polymers. In embodiments, the copper-zinc malonates can be found in several hydrate, and polymorphic forms.

In embodiments, the process parameters are especially advantageous if the polyfunctional compound is added to excess in comparison to the metal counter cation constituents. Depending on the desired complex, the latter are added so that the molar ratio of polyfunctional compound to metal ions is approximately 3:2.

Embodiments of Compositions Containing the Polymetal Complex

In embodiments, the polymetal complex formed from the resulting reaction products may serve as active ingredients in compositions suitable for anorectal administration. Such active ingredients may be combined with numerous ingredients to form a variety of products which may be capable of anorectal administration. The active ingredients in suitable toxicological compositions can be applied to the anorectal region or tissues of humans or other mammals. Such products may include a dermatologically or pharmaceutically acceptable carrier, vehicle or medium, for example, a carrier, vehicle or medium that is compatible with the tissues to which they will be applied. Some non-limiting examples include water, saline, dextrose, oil-in-water or water-in-oil emulsions. Some additional examples are described in REMINGTON'S PHARMACEUTICAL SCIENCES (Mack Publishing Company). The term "dermatologically or pharmaceutically acceptable," as used herein, means that the compositions or components thereof so described are suitable for use in contact with these tissues or for use in patients in general without undue toxicity, incompatibility, instability, allergic response, and the like. In embodiments, compositions in accordance with the present disclosure can contain any ingredient conventionally used in cosmetics and/or dermatology. In embodiments, active ingredients may be formulated to provide crystals in solution, as well as solid forms.

In embodiments, products containing a reaction product in accordance with the present disclosure as an active ingredient can be in the form of solutions, emulsions (including microemulsions), suspensions, creams, lotions, gels, powders, foams, enemas, suppositories, aerosols, sprays or other typical solid or liquid compositions used for treatment of anorectal disorders. Such compositions may contain, in addition to the reaction product in accordance with this disclosure, other ingredients typically used in such products, such as pharmaceutically active agents, moisturizers, hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents, buffers, protectants, pH regulators, chelating agents, propellants, counter-irritants, humectants, lubricants, astringents, conditioners, darkening or lightening agents, glitter, mica, minerals, silicones, polyphenols, sunblocks, phytomedicinals, and combinations thereof.

The term "pharmaceutically active agents" is meant to have the broadest interpretation as to any therapeutically active substance which is delivered to a living organism to produce a desired and often beneficial result. Some not limiting examples include antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, $H_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents and immunosuppressive agents; wound healing agents, adhesives, sealants, blood products, blood components, ultraviolet absorbers, ultraviolet stabilizers, photochromic agents, proteins, polysaccharides, peptides, genetic material, immunological agents, anti-colonization agents, diagnostic agents, imaging agents and combinations thereof.

As an illustrative example, products can be formulated to contain copper-zinc malonate in amounts from about 0.001 to about 25% by weight of the total composition. In embodiments, products can be formulated to contain copper-zinc malonate in an amount from about 0.05 to about 10% by weight of the total composition. In other embodiments, the amount of copper-zinc malonate is from about 0.1 to about 5% by weight of the total composition. Here, the copper-zinc malonate present may be in a pharmaceutically acceptable salt form. Other active ingredients may be provided in the formulations at the same concentrations.

The particular active ingredient or ingredients employed, and the concentration in the compositions, generally depends on the purpose for which the composition is to be applied. For example, the dosage and frequency of application can vary depending upon the type and severity of the anorectal disorder.

Similarly, the pH of the compositions may vary according to the form of the composition, the ingredients contained therein and the type of tissue the composition is contacting. In embodiments, the pH of the compositions may range from about 4.0 to about 10.0. In embodiments, the pH of the composition may range from about 4.5 to about 8.0 and in particularly useful embodiments, the pH of the composition may range from about 5.5 to about 6.0.

In particularly useful embodiments, the compositions may include the polymetal complex and at least one pharmaceutically active agent known to treat anorectal disorders. In one example the composition may include a polymetal complex and hydrocortisone, a drug commonly found in hemorrhoidal suppositories and creams. In other embodiments, the composition may include a polymetal complex and an anesthetic such as dibucaine, benzocaine, lidocaine and the like. In still other embodiments, the compositions may include a polymetal complex and a pain reliever such as acetaminophen, ibuprofen, codeine, and the like. Compositions which include various combinations of pharmaceutically active agents are also envisioned.

It has also been discovered that the compositions which contain the polymetal complex are useful in causing varying levels of vasoconstriction. Such an effect may be useful in many anorectal disorders. Moreover, the vasoconstrictive effect of the present compositions decrease the rate at which the body is able to clear the composition by local blood supply, thereby allowing the composition to remain at the site of application longer which increases the rate and depth of tissue penetration of the composition. In embodiments, the compositions of the present application may be combined with other vasoconstrictive agents to further enhance the effect of the polymetal complex.

Example 1 is an illustrative vasoconstrictive gel for this purpose.

EXAMPLE 1

| Ingredient | % by Weight |
| --- | --- |
| Water (Purified) | 69.3728 |
| Witch Hazel Distillate | 2.000 |
| Copper Zinc Malonate | 0.0772 |
| Phenylephrine Hydrochloride | 0.2500 |
| Yeast Cell Extract | 1.0000 |
| Potassium Sorbate | 0.3000 |
| Phenoxyethanol | 1.0000 |
| Glycerin | 20.0000 |
| Hydroxyethylcellulose (250H) | 1.0000 |
| Flush - Water (Purified) | 5.0000 |
| Sodium Hydroxide (10% w/v) | to adjust pH to 6 |

Example 2 is vasoconstrictive emulsion in accordance with an embodiment of this disclosure.

EXAMPLE 2

| Ingredient | % by Weight |
| --- | --- |
| Water (Purified) | 58.1128 |
| Glycerine | 22.0000 |
| Sorbitol (70% sol'n) | 5.0000 |
| Copper Zinc Malonate | 0.0772 |
| Phenylephrine Hydrochloride | 0.2600 |
| Sodium Hyaluronate | 2.2500 |
| Potassium Sorbate | 0.3000 |
| Phenoxyethanol | 1.0000 |
| Sepineo ® P600 (shake bottle)* | 6.0000 |
| Yeastolate, UF** | 5.0000 |
| Sodium Hydroxide (10% w/v) | to adjust pH to 6 |

*SEPINEO P600 is a 3-in-1 polymer: thickener, emulsifier and stabilizing agent commercially available from SEPPIC Inc., Fairfield, NJ USA.
**Water soluble portion of autolyzed yeast that has been ultrafiltered.

In embodiments, the compositions of the present application may be combined with vasodilating agents thereby decreasing the effect of the polymetal complex.

In embodiments, the compositions described herein may be incorporated into suppository formulations for anorectal administration. The polymetal complexes may be combined with any known suppository base material. Some examples of known suppository base materials include, but are not limited to, Fattibase™ (polyethylene glycol base), Vehicle-S™ (acrylic polymer resin base), and Polybase™ (polyethylene glycol base), cocoa butter, waxes, glycerinated gelatins, and hydrogenated vegetable oils. Such materials are readily available for preparing the present formulations and have desirable pH's, melting points, and preservatives.

The suppositories may be formed by any known process including for example, cold compression and fusion processes. In embodiments, the composition including the polymetal complex may be mixed with a suppository base material which has been heated. The composition may be a solid or liquid. Once incorporated, the mixture is poured into a mold which is well-cooled or frozen and the mixture is allowed to solidify within the mold. The solid mixture is then removed from the mold in the form a suppository.

In other embodiments, the compositions described herein may be incorporated into rectal enemas. Generally, rectal enemas are liquid compositions, solutions, emulsions or suspensions which may contain additional ingredients such as thickeners, preservatives, pH regulators, thickeners and active agents. The rectal enemas described herein may include from about 0.1 mg to about 10 mg of polymetal complex per enema.

In still other embodiments, the compositions described herein may be incorporated into rectal foams. Rectal foams may have a polymetal complex content from about 0.1 mg/dose to about 10 mg/dose. In addition, rectal foams may also include: traditional solubilizers, such as purified water and propylene glycol (the latter also acts as a thickener and is used for enemas) and solubilizers also protecting the skin, essentially consisting of partial glycerides of polyoxyethylenic saturated fatty acids; emulsifiers, such as polysorbate 20 and mixtures of cetostearylic alcohol with sorbitan esterified with polyoxyethylenic fatty acids; chelating agents, such as ethylenediaminetetraacetic acid, also in the form of sodium salt; preservatives, such as parabens—also used for enemas; acidifying buffers, such as phosphoric acid and monobasic sodium or potassium phosphate; propellants, such as hydrocarbons, e.g. isobutane, or fluorocarbons, e.g. dichlorodifluoromethane and dichlorotetrafluoroethane, or hydrochlorofluorocarbons or hydrofluorocarbons. As concerns the pharmaceutical formulation, rectal foams—compared with enemas—have a lower water content and contain propellants, which are indispensable for dispensing the dose of drug to be administered.

It is the presence of propellants that allows the dose dispensed at each release of the pressure valve—in case of multidose bottles—or on pressure release valve—in case of single-dose bottles—to spread out and reach the innermost areas of the anorectal region.

The propelling properties can vary depending on the type and quantity of propellant used and, consequently, the foam can reach more or less distant regions of the anorectal region.

Treatments in accordance with the present disclosure contact the anorectal tissue with one or more active ingredients such as those containing copper, zinc and/or silver in an effective amount to improve the undesirable anorectal disorder. In embodiments, compositions containing a polymetal complex in accordance with the present disclosure are applied externally to a hemorrhoid or in the lower portion of the anal canal. In embodiments, patients are treated by administering one or more copper-zinc malonates to a subject's anorectal region. In embodiments, patients suffering from a anorectal disorder are treated by inserting or applying to anorectal tissue, one or more salts in accordance with the present disclosure. The active ingredient is applied until the treatment goals are obtained. However, the duration of the treatment can very depending on the severity of the condition. For example, treatments can last several weeks to months depending on whether the goal of treatment is to reduce or eliminate the anorectal condition.

In embodiments, a copper-zinc carboxylic acid salt having copper and zinc cations in the same molecule is applied to anorectal tissue.

In treatment embodiments, the compositions and methods in accordance with the present disclosure can be combined with other skin or anorectal treatment systems. For example, the polymetallic salt complexes can be applied to the anorectal region of a subject in combination with another anorectal treatment option. The active ingredients and formulations in accordance with the present disclosure may either be incorporated into other product formulations, or applied to the anorectal region before, after, and/or during other anorectal treatments.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of treating an anorectal disorder comprising the step of administering to an anorectal region of a subject suffering from anal fissures, disorders associated with hemorrhoids, levator spasms, or constipation, an effective amount of a composition comprising a polymetal complex, the polymetal complex being a reaction product of a polyfunctional compound with two or more coordination elements, the polyfunctional compound being selected from the group consisting of polyfunctional amines, amino acids, maleic acid, fumaric acid, citraconic acid, itaconic acid, glutaconic acid, phthalic acid, isophthalic acid, terephthalic acid, cyclohexane dicarboxylic acid, succinic acid, adipic acid, sebacic acid, azealic acid, malonic acid, dodecanedioic acid, 1,18-octadecanedioic acid, hyaluronic acid and salts thereof, dimer acids and alkenyl succinic acids.

2. The method of claim 1 wherein the two or more coordination elements are copper and zinc.

3. The method of claim 1 wherein the polyfunctional compound is malonic acid.

4. The method of claim 1 wherein the polyfunctional compound is maleic acid.

5. The method of claim 1 wherein the polyfunctional compound is a polyfunctional amine.

6. The method of claim 1 wherein the polyfunctional compound is an amino acid.

7. The method of claim 1 wherein the polyfunctional compound is a hyaluronic acid or a sodium salt of hyaluronic acid.

8. The method of claim 6 wherein the amino acid is glutamic acid.

9. The method of claim 1 wherein the composition further includes at least one pharmaceutical carrier.

10. The method of claim 9 wherein the pharmaceutical carrier is selected from the group consisting of water, polyethylene glycol, glycerin, saline, dextrose, hydrogenated vegetable oils, gelatin, cocoa butter, and combinations thereof.

11. The method of claim 1 wherein the composition further includes a material selected from the group consisting of pharmaceutically active agents, moisturizers, hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents, buffers, protectants, pH regulators, chelating agents, propellants, counter-irritants, humectants, lubricants, astringents, conditioners, minerals, silicones, polyphenols, phytomedicinals, and combinations thereof.

12. The method of claim 1 wherein the composition is in a form selected from the group consisting of solutions, suspensions, emulsions, creams, lotions, gels, ointments, powders, foams, enemas, suppositories, sprays gel, and combinations thereof.

13. A composition comprising a polymetal complex and a carrier suitable for anorectal use, the polymetal complex being a reaction product of a polyfunctional compound with two or more coordination elements, the polyfunctional compound being selected from the group consisting of polyfunctional amines, amino acids, maleic acid, fumaric acid, citraconic acid, itaconic acid, glutaconic acid, phthalic acid, isophthalic acid, terephthalic acid, cyclohexane dicarboxylic acid, succinic acid, adipic acid, sebacic acid, azealic acid, malonic acid, dodecanedioic acid, 1,18-octadecanedioic acid, hyaluronic acid and salts thereof, dimer acids and alkenyl succinic acids, and wherein the composition is a suppository.

14. The composition of claim 13 wherein the two or more coordination elements are copper and zinc.

15. The composition of claim 13 wherein the polyfunctional compound is malonic acid.

16. The composition of claim 13 wherein the polyfunctional compound is a polyfunctional amine.

17. The composition of claim 13 wherein the polyfunctional compound is an amino acid.

18. The composition of claim 17 wherein the amino acid is glutamic acid.

19. The composition of claim 13 wherein the carrier comprises one or more members selected from the group consisting of polyethylene glycol, glycerin, saline, dextrose, hydrogenated vegetable oils, gelatin, cocoa butter, water and combinations thereof.

20. The composition of claim 13 wherein the composition further includes a material selected from the group consisting of pharmaceutically active agents, moisturizers, hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents, buffers, protectants, pH regulators, chelating agents, counter-irritants, humectants, lubricants, astringents, conditioners, minerals, silicones, polyphenols, phytomedicinals, and combinations thereof.

21. The composition of claim 13 wherein the composition is a suppository.

* * * * *